United States Patent
Alexandre et al.

(10) Patent No.: US 6,666,843 B1
(45) Date of Patent: Dec. 23, 2003

(54) NEEDLELESS SYRINGE WITH TEMPORARILY RETAINED THRUSTING MEANS

(75) Inventors: Patrick Alexandre, Gray (FR); Bernard Brouquieres, Toulon (FR); Philippe Gautier, Le Plessis Pate (FR); Denis Roller, La Ferte Alais (FR)

(73) Assignee: CrossJect, Paris (FR)

( * ) Notice: Subject to any disclaimer, the term of this patent is extended or adjusted under 35 U.S.C. 154(b) by 84 days.

(21) Appl. No.: 10/089,642

(22) PCT Filed: Oct. 23, 2000

(86) PCT No.: PCT/FR00/02943
§ 371 (c)(1),
(2), (4) Date: May 1, 2002

(87) PCT Pub. No.: WO01/32243
PCT Pub. Date: May 10, 2001

(30) Foreign Application Priority Data

Nov. 5, 1999 (FR) .......................................... 99 13850

(51) Int. Cl.[7] .................................................. A61M 5/30
(52) U.S. Cl. ............................................ 604/69; 604/68
(58) Field of Search ........................ 604/69, 68, 82–89, 604/143, 181, 187, 244

(56) References Cited

U.S. PATENT DOCUMENTS

| | | | |
|---|---|---|---|
| 2,322,245 A | 6/1943 | Lockhart | |
| 3,802,430 A | 4/1974 | Schwebel et al. | |
| 4,124,024 A | 11/1978 | Schwebel et al. | |
| 5,630,796 A | * 5/1997 | Bellhouse et al. | .......... 604/518 |
| 6,406,455 B1 | * 6/2002 | Willis et al. | .................. 604/68 |

FOREIGN PATENT DOCUMENTS

| | | |
|---|---|---|
| EP | 0 888 790 A1 | 1/1999 |
| WO | WO 97/13537 A1 | 4/1997 |

* cited by examiner

Primary Examiner—Manuel Mendez
Assistant Examiner—Kevin C. Sirmons
(74) Attorney, Agent, or Firm—Oliff & Berridge, PLC

(57) ABSTRACT

The invention concerns the field of needless syringe for injecting liquid active principle for therapeutic purposes. It concerns a syringe wherein the active principle (1, 10) is initially placed between an injector (2, 22) comprising at least an injection duct (3, 23) contacted with the skin and a mobile wall (4, 24) separated from thrusting means (5, 25) displaced by gases of propellant generator (7, 27) pressurising and expelling the active principle. Said syringe aims at quickly providing a high expelling speed of the liquid to efficiently perforate the skin and improve bioavailability. Said syringe is characterised in that said thrusting means (5, 25) comprising temporary retention device (6, 26) deactivated by the operation of the propellant generator (7, 27).

9 Claims, 2 Drawing Sheets

NEEDLELESS SYRINGE WITH TEMPORARILY RETAINED THRUSTING MEANS

The present invention concerns the field of needleless syringes used for intradermal, subcutaneous or intramuscular injections of liquid active principle for therapeutic use in human or veterinary medicine.

A needleless syringe is noninvasive by definition: there is no needle passing through the skin in order to bring the active principle to the place where it is to act. For a needleless syringe, it is necessary for the jet of liquid active principle emerging from an orifice or injection conduit to pierce the skin and penetrate to a greater or lesser depth depending on the type of injection desired: to do so, the jet must have a high speed. If the jet is too slow, there is no perforation of the skin, the liquid spreads across the surface of the skin, and it is lost because it produces no therapeutic effect.

In most syringes, the devices for delivering the liquid active principle through the injector are generally displaceable walls of the piston type or of the deformable membrane type which have to be displaced or deformed rapidly, with great acceleration, in order to quickly produce a high-speed jet for piercing the skin.

In patent U.S. Pat. No. 2,322,245, Lockhart describes needleless syringes whose displaceable wall is displaced or driven either by a compressed mechanical spring or by a compressed gas reserve. This drive device acts directly on a rod which impacts a delivery piston situated at a relatively large distance therefrom; the rod is accelerated over this distance by the release of the spring, it impacts the delivery piston, sets it in motion and displaces it quickly enough to atomize the active principle through quite a fine conduit and inject it.

By contrast, for syringes with a pyrotechnic drive, which are described in the same patent, or patents U.S. Pat. No. 3,802,403 and U.S. Pat. No. 4,124,024, the pyrotechnic charge acts directly on the delivery piston or by way of a bellows resting on said piston.

More recently, the patent application WO 95/03844, concerning needleless syringes, again takes up basically the same technique of an impact rod acting on a delivery piston. The impact rod is driven by a mechanical spring or a compressed gas reserve. The drive device is in a high-energy state, and it acts directly on the impact rod which is retained by a lock thereby preventing release of the spring or the compressed gas. During the whole storage period prior to use, the rod and the lock are greatly prestressed.

Opening said lock, directly or by way of a cam, releases the impact rod and the stored energy, which displace the movable components, and injects the liquid. The system changes from a high-energy level to a low-energy level at the end of injection. For disposable syringes, return to the initial state is not possible. Those syringes which are to be used several times comprise auxiliary devices for recompressing the spring and refilling the reservoir of liquid active principle or changing it.

Likewise, patent application WO 97/13537 describes a needleless syringe comprising a displaceable wall and a thrust means consisting of a rod with a piston head. The thrust means is set in motion when the force resulting from the gas pressure of the generator on the piston head is greater than the force resulting from the friction of the piston; the temporary retention thus realized by this equilibrium of the forces translates into quite a slow movement of the displaceable wall.

These devices have several disadvantages. The bioavailability obtained by these devices is not entirely satisfactory. Note that bioavailability is defined by the quantity of liquid actually injected in relation to the quantity initially filling the reservoir of the syringe.

These devices are cumbersome and heavy since they need to be large enough to permit a relatively long course of travel for acceleration of the impact rod. Moreover, spring or compressed gas motors provided for storing a high level of energy for a considerable time prior to use will be structurally quite heavy. Moreover, these devices have problems relating to reliability. In the case of prolonged storage: the spring compressed to the maximum extent degrades; the compressed gas supply will be subject to leaks, and the highly prestressed lock may also experience operating difficulties. In all cases, these devices will be overdimensioned in an attempt to remedy the stated problems of reliability and they will therefore be a little more cumbersome and a little heavier.

The object of the invention is to increase the bioavailability of the active principle by improving the phase of acceleration of the liquid, and also to make available devices which are more compact and reliable.

The present invention concerns a needleless syringe for injection of a liquid active principle initially placed between, on the one hand, an injector comprising at least one injection conduit, said injector being placed in contact with the skin or in immediate proximity to the skin of the subject to be treated, and, on the other hand, a displaceable wall initially separated from a thrust means displaced by the gases from a gas generator and ensuring the pressurization and expulsion of the liquid active principle through the injector placed at the downstream end of the syringe, said syringe being such that said thrust means includes a temporary retention device deactivated by the functioning of the gas generator initiated by a trigger member.

The thrust means is initially separated from the displaceable wall by a short distance which is determined in a manner which we will explain below. The functioning of the gas generator deactivates the temporary retention means, abruptly displaces the thrust means to bring it into contact with the displaceable wall, thereby ensuring very rapid pressurization of the liquid and its injection at high speed. More precisely, the operator acts on a member which triggers the functioning of the gas generator, these latter acting on the thrust means and in doing so deactivating the temporary retention device of said thrust means. By contrast, in the devices of the prior art, the operator acts (directly or indirectly) on a lock, which is a retention device, in order to release the energy necessary for the functioning of the device.

In this invention, liquid active principle will be understood essentially as a more or less viscous liquid, or a mixture of liquids, or a gel. The active principle will be able to be solid in the form of a powder in more or less concentrated suspension in a suitable liquid. The granulometry of the solid and pulverulent active principle must be adapted, as must the shape of the conduit, to avoid blocking of the conduits.

Advantageously for this syringe, the temporary retention device will be breakable: it will be broken upon functioning of the gas generator. Said temporary retention system will be calibrated, that is to say the rupture of the breakable temporary retention device will occur only when the thrust means is subjected, by the effect of the gases from the generator, to a given force, depending in particular on the active principle and on the conditions of use, in order to very quickly obtain a jet of liquid moving at high speed.

Preferably in this syringe the initial distance separating the thrust means from the displaceable wall will be greater than the maximum deformation, before rupture, of the temporary retention device. By observing this condition, the thrust means does not come into contact with the displaceable wall upon deformation of the temporary retention device: there is therefore no liquid delivered at very low speed during the deformation of the breakable temporary retention device.

The initial distance separating the thrust means from the displaceable wall advantageously remains small in order to limit the size of the syringe. Said distance is at most of the order of magnitude of a notable dimension of the thrust means which determines the force acting on the breakable temporary retention device. For example, said distance will remain less than about one tenth of the diameter or of the equivalent diameter of the thrust means.

The gas generator driving the syringe is preferably a pyrotechnic gas generator. This type of gas generator comprises, prior to functioning, a pyrotechnic charge in solid or possibly powder form, a device for initiating the combustion of said charge, and a member for triggering said initiation device. Contrary to the case of a compressed spring, the triggering member is not subjected to any prestressing.

The temporary retention device is advantageously chosen from the group including pins: simple shearable pins or pins with zones of weakening, breakable studs; shearable protective caps which will be sheared in a circle if the thrust means is circular, shearable flanges.

The temporary retention device can also advantageously be an axial rod of which one end is fixed to the thrust means and the other end is fixed to a suitable device on the gas generator side. The rupturing of this axial rod takes place by elongation; this rupture can be controlled by means of a suitably weakened zone of the rod.

To fulfill the function of breakable temporary retention device, it may be possible to use retention devices which are deactivated by deformation or displacement of certain elements; for example, devices with catches which will be deformed or with pawls which will be displaced when said devices are subjected to a substantial and predetermined stress applied to the thrust means.

The thrust means will also advantageously be a piston, in order to limit the size of the device. This piston comprises sealing devices, for example an O-ring seal to ensure correct functioning thereof and to avoid gas leaks toward the active principle reservoir.

In a first embodiment, the displaceable wall will also be a piston, a delivery piston, with sealing devices to form a second level of sealing. By choosing suitable materials for the thrust means and the displaceable wall, it is possible to some extent to control the force of the impact of the two components.

In this embodiment, the pistons constituting the thrust means and the delivery piston have equal or different diameters. However, when the thrust means has a diameter greater than that of the delivery piston, said thrust means has, in its downstream part, a protruding portion whose diameter is at most equal to that of the delivery piston, the length of this protrusion being greater than the course of travel of the thrust means.

In a second embodiment, the displaceable wall will be a deformable membrane. This membrane, preferably thin, will be made of metal or elastomer or plastic material; these materials will be compatible with the active principle. The fixation of said membrane in the syringe will ensure its sealing. This fixation will be achieved, for example, by pinching, crimping or overmolding.

In this embodiment, the downstream face of the thrust means has a shape which is adapted to stamp and deform the deformable membrane on the inner face of the injector so that, at the end of injection, the deformed membrane is sandwiched between the downstream face of the thrust means and the inner face of the injector in order to completely empty the active principle reservoir. We will note that the downstream face of the thrust means and the inner face of the injector have matching shapes.

On account of the power available with a pyrotechnic gas generator and the breakable temporary retention device, a high-speed jet is very quickly obtained for perforating the skin, and the bioavailability of the active principle is thus improved.

The size and the weight of the syringe are reduced by the limitation of the displacement of the thrust means toward the displaceable wall. The compactness of a pyrotechnic gas generator adds further to this effect.

Finally, the reliability of the pyrotechnic gas generators is excellent; in particular, throughout the phase between assembly and use, no element of the pyrotechnic gas generator is subjected to prestressing.

Another advantage of this syringe is linked to the separation of the thrust means and the displaceable wall: it is possible to differentiate between two subassemblies in the syringe. The first one contains the active principle, it is prepared and packaged under the conditions pertaining in the pharmaceutical industry, and the other contains the gas generator, and it too is prepared and packaged under the conditions pertaining to this type of apparatus. The two subassemblies are joined together in a work area in which regulatory and technical constraints are very limited.

The invention is explained in greater detail below and with reference to figures representing particular embodiments.

To facilitate the descriptions, the syringes will be assumed to be vertical with their downstream part directed toward the bottom.

Figure 1:
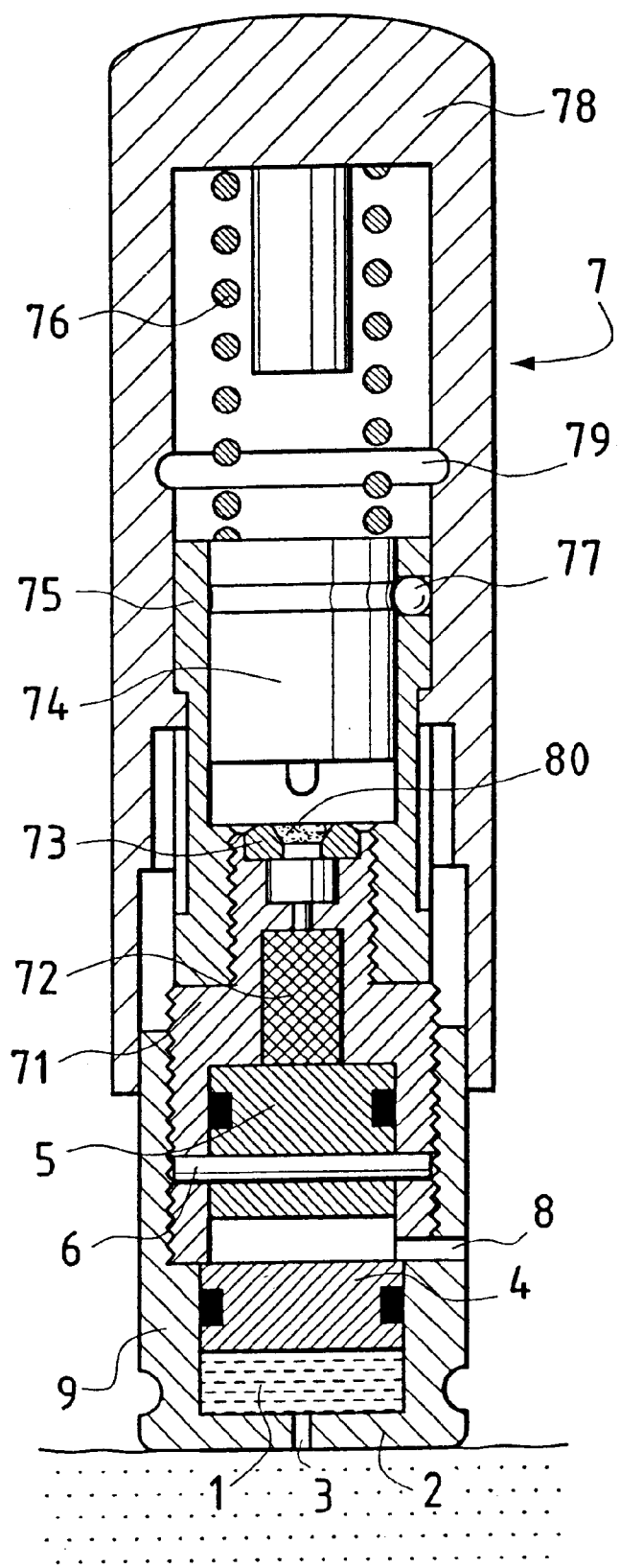
FIG. 1 is a schematic and partially cutaway view of a first embodiment of the syringe with a thrust piston and a delivery piston.

FIG. 1 shows, in partial longitudinal section, a needleless syringe according to the invention. The downstream part 9 of the syringe comprises an injector 2 with a single injection conduit 3 in this example. The injector 2 rests on the skin of the subject to be treated. The liquid active principle 1 is situated in the reservoir formed by the inner part of the downstream part 9 of the syringe closed by the delivery piston 4. The delivery piston 4 comprises an O-ring seal to ensure leaktightness. Situated in the body 71, fixed by screwing on the downstream part 9, is the thrust means, in this case a piston 5, with an O-ring seal to ensure leaktightness. Said piston 5 is held temporarily in place by a pin 6 which extends through the piston and the body 71. In this example, the thrust piston 5 has a diameter slightly smaller than that of the delivery piston 4, the thrust piston does not require any particular arrangement, such as we have described it before, to ensure correct functioning. The thrust piston 5 is placed a short distance from the delivery piston 4. This distance is greater than the maximum deformation of the pin before rupture. The piston 5 during this slow deformation does not come into contact with the piston 4 and there is therefore no liquid delivered at low speed. The piston 5 is at a distance equal to about twice the diameter of the pin in order to limit this distance and reduce the overall size.

The volume situated between the thrust piston 5 and the delivery piston 4 can communicate with the outside via at least one vent, such as the vent 8, this vent being drilled through the downstream part 9 and the body 71 and serving to evacuate the air from between the two pistons during functioning.

In this example, the piston 5 is displaced by a pyrotechnic gas generator 7 whose main elements we will now describe. The pyrotechnic gas generator 7 comprises, in the body 71 above the drive piston 5, a pyrotechnic charge 72 whose combustion is initiated by a primer 80 impacted by a striker 74, which striker is not represented in cross section but is seen from the side. The primer 80 is lodged in a primer holder 73. In the initial position the striker 74 is held in the striker guide 75, made integral with the body 71 by screwing, via at least one ball, such as the ball 77, partially engaged in a groove of the striker. The strike device comprises a pusher 78 with a groove 79 and an inner spring 76.

The pusher 78 slides on the outside of the striker guide 75 and it is held by studs which are displaced in lateral channels. This pusher 78 is in this case the triggering member.

Of course, in order to initiate the combustion of the pyrotechnic charge 72, and without departing from the scope of the invention, it is possible to use initiation devices other than the striker device described here. Without going into details and without seeking to be exhaustive, we will mention as examples initiator devices with an electric battery or piezoelectric initiator devices.

If appropriate, the pyrotechnic gas generator can be replaced by a gas generator formed by a compressed gas reservoir closed by a valve which opens rapidly. The triggering member will open said valve, and the compressed gases of the reservoir will be released and act on the thrust means in order to deactivate the temporary retention device and accelerate the thrust means and displace it with the displaceable wall in order to perform the injection.

In FIG. 1, the syringe is ready for use, resting on the skin of the subject who is to be treated. The operator presses his thumb on the pusher 78 which moves downward and compresses the spring 76. The pusher is displaced until the groove 79 arrives at the level of the groove in the striker 74, and the balls, such as the ball 77 retaining the striker 74, escape into the groove 79 and free the striker which impacts violently on the primer 80 whose initiation ignites the pyrotechnic charge 72. The striker resting on the primer holder 73 ensures leaktightness: the gases of combustion do not rise back toward the pusher.

The combustion of the pyrotechnic charge will produce gases which act on the thrust piston 5. The pressure above this piston increases until the resulting force is sufficient to shear the pin 6. When the pin 6 breaks, the thrust piston 5 is very rapidly accelerated as it is subjected to a considerable force. The thrust piston 5 impacts the delivery piston 4 and displaces it very rapidly. The liquid active principle 1 is ejected through the conduit 3 of the injector 2 at high speed: it easily pierces the skin and spreads to a greater or lesser depth through the latter. The kinetics of combustion of the pyrotechnic charge 72 and the calibration of the pin 6 make it possible to regulate the speed of the liquid jet.

In a more elaborate embodiment, the pin, made from a material more resistant to shearing, has two weakened sections in line with the outer surface of the thrust piston. The breaks of the pin will be of smaller cross sections and will have less effect on the functioning of the thrust piston. The notches, corresponding to the zones of weakened cross sections, are dimensioned so that the rupture occurs at the same pressure as with a simple pin made of a less resistant material.

For the temporary and breakable retention system, the thrust piston, the body 71 and the pin 6 will preferably be made of metal, for example of suitable steels. The delivery piston 4, in contact with the liquid active principle, will be made of a metal or plastic material or elastomer compatible with said active principle.

The pyrotechnic charge is made, for example, from a nitrocellulose-based powder, a powder whose granulometry is chosen to give suitable kinetics of combustion, for example 120 mg of BTu powder according to the SNPE catalog which permits shearing of a rigid steel pin of 1.5 mm diameter at a pressure of 9 MPa on a piston of 12 mm diameter.

FIG. 1 can also be explained in terms of the advantage afforded by the use of a thrust piston 5 separated from a delivery piston 4 or, more generally, a thrust means separated from a displaceable wall. The syringe can be separated into two subassemblies. The first subassembly will comprise the downstream part 9 of the syringe containing the liquid active principle 1 and closed by the delivery piston 4: this subassembly can be assembled and filled in a work area complying with the standards of pharmaceutical manufacture, particularly from the point of view of asepsis; the asepsis of the downstream face of the injector 2 must be protected by a suitable stopper which will also avoid losses of liquid during the maneuvers which follow filling. The second subassembly is obtained by preparation and assembly in a work area complying with the standards of pyrotechnics, this subassembly will be suitably secured to prevent displacements of the pusher which would cause inadvertent functioning of the gas generator. Its two subassemblies prepared separately will finally be joined together, in an environment requiring fewer precautions, to form the complete syringe; it will then be packaged for delivery to customers.

Figure 2:
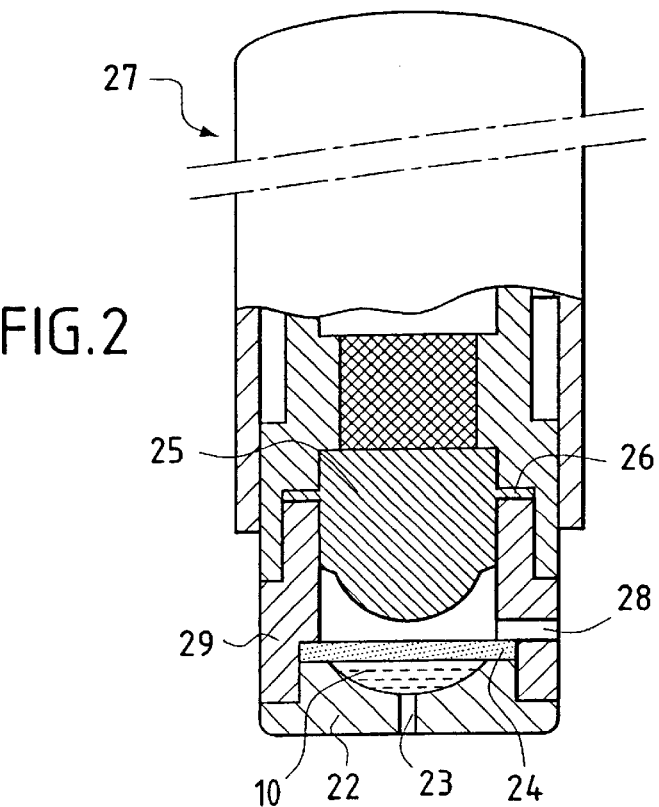
FIG. 2 is a partial cutaway view of a second embodiment with a thin deformable membrane.

FIG. 2 shows another embodiment of a syringe according to the invention. It differs from the previous one particularly in terms of the shape of the thrust piston, the temporary retention device and the displaceable wall.

This figure shows an injector 22 with an injection conduit 23. The inner part of the injector has substantially the shape of a spherical cap; it contains the liquid active principle 10, a thin deformable membrane 24 closes the reservoir. In this example, the thin membrane is pinched between the injector 22 and the guide piece 29. The thin deformable membrane 24 can also be crimped or overmolded on the injector 22. Situated above this deformable membrane, the thrust piston 25 is held by a breakable flange 26 pinched between the guide piece 29 and the body of the gas generator. The thrust piston 25 has, on its downstream face toward the thin deformable membrane 24, a spherical cap shape matching that of the injector. The distance separating the thrust piston 25 from the thin deformable membrane is less than twice the thickness of the breakable flange 26. In this figure, the thicknesses of the thin deformable membrane 24 and of the breakable flange 26 have been exaggerated for the purposes of clarity of the drawing.

In this example, the matching shapes of the front face of the thrust piston and the inner face of the injector are spherical caps, but more elaborate shapes are also conceivable.

The thrust piston is displaced by a pyrotechnic gas generator, labeled 27; this generator is identical to that in the example, and its description will not be detailed again.

When the combustion of the pyrotechnic charge is initiated, the gases produced will increase the pressure on the upstream face of the thrust piston 25 until the resulting force shears the flange, and the thrust piston 25 is very rapidly accelerated since it is subjected to a considerable force. The thrust piston 25 impacts the deformable membrane 24 and stamps it against the inner face of the injector 22 and in doing so the active principle is ejected through the conduit 23 of the injector 22 at a high speed, as in the previous example.

Figure 3:
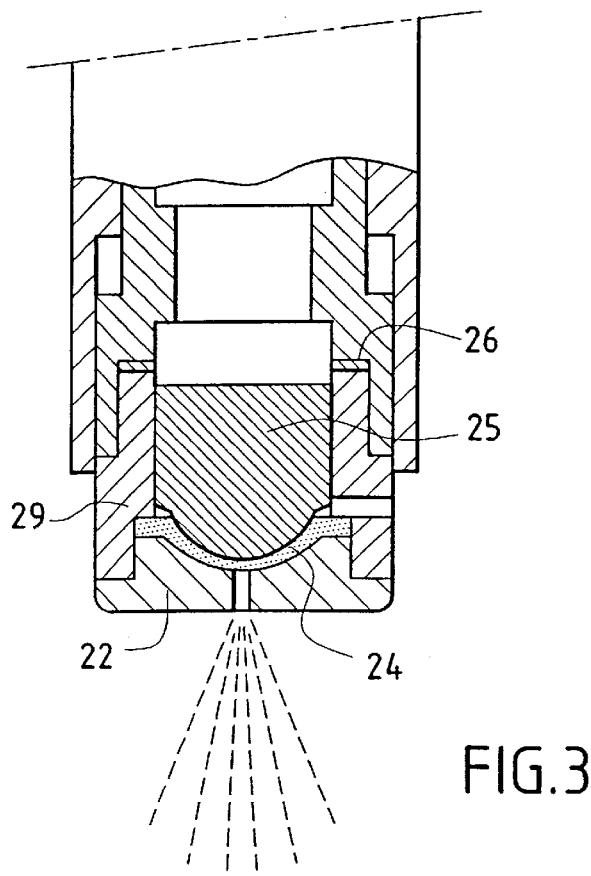
FIG. 3 shows the detail of the downstream part of the above syringe after use.

FIG. 3 shows schematically the downstream part of the syringe of the above example at the end of functioning. The pyrotechnic charge has burned out completely. The flange 26 of the piston has sheared about a circumference, and it remains between the pieces 29 and 71. The thrust piston 25 has stamped and deformed the deformable membrane 24.

What is claimed is:

1. A needleless syringe comprising a gas generator (7, 27) forcing said syringe, wherein said syringe is for injection of a liquid active principle (1, 10) contained in a reservoir inside the downstream part (9, 29) of said syringe, said reservoir having, at the downstream end, an injector (2, 22) with at least one injection conduit (3, 23) and, at the opposite end, a displaceable wall (4, 24), said displaceable wall being separated from a thrust means (5, 25) which has a calibrated temporary retention device, characterized in that said temporary retention device is a breakable device (6, 26).

2. The needleless syringe as claimed in claim 1, characterized in that the initial distance separating the thrust means (5, 25) from the displaceable wall (4, 24) is greater than the maximum deformation before rupture of the breakable temporary retention device (6, 26).

3. The needleless syringe as claimed in claim 1, characterized in that the initial distance separating the thrust means (5, 25) from the displaceable wall (4, 24) is less than about one tenth of the diameter of the thrust means.

4. The needleless syringe as claimed in claim 1, characterized in that the gas generator (7, 27) is a pyrotechnic gas generator.

5. The needleless syringe as claimed in claim 1, characterized in that the temporary retention device (6, 26) is chosen from the group including in particular pins and protective caps.

6. The needleless syringe as claimed in claim 1, characterized in that the thrust means (5, 25) is a piston.

7. The needleless syringe as claimed in claim 1, characterized in that the displaceable wall (4) is a delivery piston.

8. The needleless syringe as claimed in claim 1, characterized in that the displaceable wall (24) is a deformable membrane.

9. The needleless syringe as claimed in claim 8, characterized in that the downstream face of the thrust means (25) and the inner face of the injector (22) have matching shapes.

* * * * *